(12) United States Patent
Kitamura

(10) Patent No.: US 9,107,834 B2
(45) Date of Patent: Aug. 18, 2015

(54) BRIGHT PIGMENT AND COSMETIC COMPOSITION USING THE SAME

(75) Inventor: Takeaki Kitamura, Tokyo (JP)

(73) Assignee: Nippon Sheet Glass Company, Limited, Tokyo (JP)

( * ) Notice: Subject to any disclaimer, the term of this patent is extended or adjusted under 35 U.S.C. 154(b) by 481 days.

(21) Appl. No.: 12/596,038

(22) PCT Filed: Apr. 18, 2008

(86) PCT No.: PCT/JP2008/057638
§ 371 (c)(1),
(2), (4) Date: Oct. 15, 2009

(87) PCT Pub. No.: WO2008/130040
PCT Pub. Date: Oct. 30, 2008

(65) Prior Publication Data
US 2010/0129412 A1    May 27, 2010

(30) Foreign Application Priority Data
Apr. 18, 2007 (JP) ................. 2007-109718

(51) Int. Cl.
| A61K 8/11 | (2006.01) |
| A61Q 1/02 | (2006.01) |
| A61K 8/26 | (2006.01) |
| A61K 8/19 | (2006.01) |
| A61K 8/29 | (2006.01) |
| A61Q 1/04 | (2006.01) |
| A61Q 1/06 | (2006.01) |
| A61Q 1/10 | (2006.01) |
| A61Q 3/02 | (2006.01) |
| C09C 1/00 | (2006.01) |

(52) U.S. Cl.
CPC ... *A61K 8/19* (2013.01); *A61K 8/29* (2013.01); *A61Q 1/02* (2013.01); *A61Q 1/04* (2013.01); *A61Q 1/06* (2013.01); *A61Q 1/10* (2013.01); *A61Q 3/02* (2013.01); *C09C 1/0015* (2013.01); *C09C 1/0021* (2013.01); *C09C 1/0024* (2013.01); *C09C 1/0036* (2013.01); *A61K 2800/43* (2013.01); *A61K 2800/434* (2013.01); *C01P 2004/61* (2013.01); *C09C 2200/102* (2013.01); *C09C 2200/1025* (2013.01); *C09C 2200/301* (2013.01); *C09C 2200/302* (2013.01); *C09C 2200/303* (2013.01); *C09C 2200/304* (2013.01); *C09C 2200/307* (2013.01); *C09C 2210/50* (2013.01); *C09C 2220/10* (2013.01)

(58) Field of Classification Search
None
See application file for complete search history.

(56) References Cited

U.S. PATENT DOCUMENTS

| 3,370,971 A | 2/1968 | Linton |
| 3,391,995 A * | 7/1968 | Kowalski et al. ............. 423/555 |
| 3,483,009 A | 12/1969 | Willis |
| 3,497,374 A | 2/1970 | Nix |
| 3,545,994 A | 12/1970 | Lott |
| 3,585,160 A | 6/1971 | Miller et al. |
| 3,711,433 A | 1/1973 | Willey et al. |
| 4,084,983 A | 4/1978 | Bernhard et al. |
| 4,239,548 A | 12/1980 | Barnard et al. |
| 4,375,373 A | 3/1983 | Abe et al. |
| 4,544,415 A | 10/1985 | Franz et al. |
| 5,183,504 A | 2/1993 | Kuwajima et al. |
| 5,223,034 A | 6/1993 | Nitta et al. |
| 5,423,912 A | 6/1995 | Sullivan et al. |
| 5,436,077 A | 7/1995 | Matsuba et al. |
| 5,472,491 A | 12/1995 | Duschek et al. |
| 5,472,734 A * | 12/1995 | Perrotta et al. ................. 427/2.1 |
| 5,668,077 A | 9/1997 | Klopries et al. |
| 5,734,068 A | 3/1998 | Klopries et al. |
| 5,753,371 A | 5/1998 | Sullivan et al. |
| 5,759,255 A | 6/1998 | Venturini et al. |
| 5,874,072 A | 2/1999 | Alwattari et al. |
| 5,958,125 A | 9/1999 | Schmid et al. |
| 5,985,258 A | 11/1999 | Alwattari et al. |
| 6,033,466 A | 3/2000 | Ito |
| 6,267,810 B1 | 7/2001 | Pfaff et al. |
| 6,348,533 B1 | 2/2002 | Kishimoto et al. |

(Continued)

FOREIGN PATENT DOCUMENTS

| DE | 24 29 762 | 1/1976 |
| DE | 41 38 376 | 9/1993 |

(Continued)

OTHER PUBLICATIONS

JP2006241012 English Abstract and Machine Translation.*

(Continued)

*Primary Examiner* — Bethany Barham
*Assistant Examiner* — Melissa Javier
(74) *Attorney, Agent, or Firm* — Hamre, Schumann, Mueller & Larson, P.C.

(57) ABSTRACT

The bright pigment of the present invention contains a scaly substrate 10 and an outermost coating 20 that covers the scaly substrate 10, that is provided as an outermost layer, and that contains at least one member selected from the group consisting of hydroxyapatite and hydrocalumite. The bright pigment of the present invention may be further provided with an interference color coating that is disposed more towards the center than the outermost coating and that contains at least one metal oxide selected from the group consisting of titanium oxide and iron oxide. Moreover, the bright pigment of the present invention may be further provided with a silver-containing coating that is disposed more towards the center than the outermost coating and that contains silver and/or a silver alloy. The outermost coating may contain an anionic pigment.

9 Claims, 1 Drawing Sheet

(56) References Cited

U.S. PATENT DOCUMENTS

| | | | |
|---|---|---|---|
| 6,488,867 B1 | 12/2002 | Matsumoto et al. | |
| 6,491,932 B1 | 12/2002 | Ramin et al. | |
| 6,533,858 B1 * | 3/2003 | Cacace et al. | 106/416 |
| 6,620,868 B1 | 9/2003 | Wilke | |
| 6,630,018 B2 | 10/2003 | Bauer et al. | |
| 6,783,584 B2 * | 8/2004 | Takahashi | 106/403 |
| 6,821,333 B2 * | 11/2004 | Zimmermann et al. | 106/405 |
| 6,929,690 B2 | 8/2005 | Vogt et al. | |
| 7,413,599 B2 | 8/2008 | Henglein et al. | |
| 8,088,211 B2 | 1/2012 | Hashizuma et al. | |
| 2002/0031534 A1 | 3/2002 | Horino | |
| 2002/0064664 A1 | 5/2002 | Kishimoto et al. | |
| 2002/0096087 A1 | 7/2002 | Glausch | |
| 2003/0105201 A1 | 6/2003 | Auschra et al. | |
| 2003/0129149 A1 * | 7/2003 | Pike et al. | 424/57 |
| 2003/0166755 A1 | 9/2003 | Muhlebach et al. | |
| 2004/0134385 A1 | 7/2004 | Anselmann et al. | |
| 2004/0143032 A1 | 7/2004 | Auschra et al. | |
| 2004/0191198 A1 | 9/2004 | Hochstein et al. | |
| 2005/0004317 A1 | 1/2005 | Auschra et al. | |
| 2005/0014865 A1 | 1/2005 | Bagala et al. | |
| 2005/0257716 A1 * | 11/2005 | Mazzella et al. | 106/400 |
| 2006/0155007 A1 | 7/2006 | Huber | |
| 2006/0159634 A1 | 7/2006 | Heinrichs | |
| 2006/0159635 A1 | 7/2006 | Meyer et al. | |
| 2006/0223910 A1 | 10/2006 | Bagala | |
| 2007/0015012 A1 | 1/2007 | Bujard et al. | |
| 2007/0032573 A1 * | 2/2007 | Yanagase et al. | 523/200 |
| 2007/0212487 A1 | 9/2007 | Anselmann et al. | |
| 2007/0299196 A1 | 12/2007 | Ohkoshi et al. | |
| 2008/0306021 A1 * | 12/2008 | Buerger et al. | 514/54 |
| 2010/0047300 A1 | 2/2010 | Kaupp et al. | |
| 2010/0083872 A1 | 4/2010 | Kitamura et al. | |
| 2010/0137488 A1 | 6/2010 | Kitamura et al. | |
| 2010/0227181 A1 | 9/2010 | Kitamura | |
| 2010/0249304 A1 | 9/2010 | Kitamura et al. | |

FOREIGN PATENT DOCUMENTS

| | | | |
|---|---|---|---|
| DE | 19739124 | 6/1998 | |
| EP | 0 191 292 | 8/1986 | |
| EP | 0 342 533 | 5/1989 | |
| EP | 0 649 886 | 4/1995 | |
| EP | 0 882 673 | 12/1998 | |
| EP | 1 469 042 | 10/2004 | |
| EP | 1 671 956 | 6/2006 | |
| JP | 46-009555 | 3/1971 | |
| JP | 48-032415 | 10/1973 | |
| JP | 55-018469 | 5/1980 | |
| JP | 60-092359 | 5/1985 | |
| JP | 61-161212 | 7/1986 | |
| JP | 1-138270 | 5/1989 | |
| JP | 1-292067 | 11/1989 | |
| JP | 1-313575 | 12/1989 | |
| JP | 3-054126 | 3/1991 | |
| JP | 3-066764 | 3/1991 | |
| JP | 4-025582 | 1/1992 | |
| JP | 4-193725 | 7/1992 | |
| JP | 6-319996 | 11/1994 | |
| JP | 7-018199 | 1/1995 | |
| JP | 7-268241 | 10/1995 | |
| JP | 08-199098 | 8/1996 | |
| JP | 10-81837 | 3/1998 | |
| JP | 10-114867 | 5/1998 | |
| JP | 10-158572 | 6/1998 | |
| JP | 10-508599 | 8/1998 | |
| JP | 10-259317 | 9/1998 | |
| JP | 10-292152 | 11/1998 | |
| JP | 11-012426 | 1/1999 | |
| JP | 11-130975 | 5/1999 | |
| JP | 2000-505833 | 5/2000 | |
| JP | 2000-169122 | 6/2000 | |
| JP | 2001-31421 | 2/2001 | |
| JP | 2001-072933 | 3/2001 | |
| JP | 2001-89324 | 4/2001 | |
| JP | 2001-226601 | 8/2001 | |
| JP | 2001-234090 | 8/2001 | |
| JP | 2002-20218 | 1/2002 | |
| JP | 2002-509561 | 3/2002 | |
| JP | 2002-114934 | 4/2002 | |
| JP | 2002-155240 | 5/2002 | |
| JP | 2002-194247 | 7/2002 | |
| JP | 2002-200844 | 7/2002 | |
| JP | 2003-12461 | 1/2003 | |
| JP | 2003-213156 | 7/2003 | |
| JP | 2004-512394 | 4/2004 | |
| JP | 2004-262794 | 9/2004 | |
| JP | 2004-275972 | 10/2004 | |
| JP | 2004-533510 | 11/2004 | |
| JP | 2005-187782 | 7/2005 | |
| JP | 2006-176742 | 7/2006 | |
| JP | 2006-192384 | 7/2006 | |
| JP | 2006-257176 | 9/2006 | |
| JP | 2006241012 | * 9/2006 | |
| JP | 2006-282572 | 10/2006 | |
| JP | 2006-328182 | 12/2006 | |
| JP | 2007-51110 | 3/2007 | |
| JP | 2007-063127 | 3/2007 | |
| JP | 2007-077297 | 3/2007 | |
| JP | 2007-138053 | 6/2007 | |
| JP | 2007-217319 | 8/2007 | |
| JP | 2007-217495 | 8/2007 | |
| JP | 2007217495 | * 8/2007 | C09C 3/06 |
| WO | 96/14278 | 5/1996 | |
| WO | 99/62646 | 12/1999 | |
| WO | 02/31058 | 4/2002 | |
| WO | 02/090448 | 11/2002 | |
| WO | 03/006558 | 1/2003 | |
| WO | 2007/054379 | 5/2007 | |

OTHER PUBLICATIONS

Sun, et al., "Preparation and Characterization of the Mica Titanium Optical Interferential Pigment Coated by $Nd_2O_3$", Bulletin of the Chinese Ceramic Society, vol. 25, No. 6, Dec. 2006—5 pages.

Kurata et al. "Saishin Funtai Bussei Zusetsu (Physical Properties of Powder Particles with Illustrations, Latest version), Third Edition," NGT Co., Jun. 30, 2004, p. 13, with its partial translation.

* cited by examiner

BRIGHT PIGMENT AND COSMETIC COMPOSITION USING THE SAME

TECHNICAL FIELD

The present invention relates to a bright pigment and a cosmetic composition in which the bright pigment is used.

BACKGROUND ART

Conventionally known bright pigments include scaly aluminium particles, graphite particles, scaly glass particles, silver-coated scaly glass particles, natural mica particles coated with a metal oxide such as titanium dioxide or iron oxide, silica particles, alumina particles, and the like.

Such bright pigments reflect light on their surface and have glitter properties and, therefore, are used as ingredients in paint, ink, resin compositions, cosmetics, and the like. A coating formed with a cosmetic that contains such bright pigments gives, in combination with the color tone of a base material of the surface, a varied, unique appearance with excellent aesthetic properties.

In particular, the following materials are known as bright pigments that have metallic luster:
(1) aluminium powder or powder obtained by pulverizing a foil-shaped, metal-coated resin, and
(2) metal-coated natural mica powder.

These bright pigments enable, due to their metallic luster, intense brightness to be given to an object to which such pigments are applied and enable an elaborately-designed appearance to be given to the object.

In synthetic mica-based pearlescent pigments, to superimpose another color on the interference color created by a colorless metal oxide coating layer, an inorganic coloring component such as iron oxide is added to the metal oxide coating layer, or the metal oxide coating layer is coated with a coating containing an inorganic coloring agent or an organic coloring agent. The colorless metal oxide coating layer is composed of a material with a high refractive index, such as titanium oxide or zirconium oxide. Thereby, a pearlescent pigment colored, for example, gold, dark blue or carmine can be obtained.

Moreover, in some cases a pigment is colored by coating a metal oxide coating layer with an anionic pigment-containing coating. In such a case, an aluminium hydroxide coating is formed in advance, and the coating is impregnated with an acidic dye for laking (for example, see Patent Documents 1 and 2). Moreover, a coloring layer also can be formed by, while simultaneously forming a coating made of anion-exchanging hydrotalcite (layered double hydroxide), intercalating an acidic dye into this coating (for example, see Patent Documents 3 and 4).

A makeup cosmetic containing scaly glass particles coated with a silver or nickel alloy-containing coating also already has been disclosed (for example, see Patent Document 5).

A method for producing particles coated with amorphous calcium phosphate (ACP, $Ca_3(PO_4)_2 \cdot nH_2O$) in which pearlescent scaly glass is coated with amorphous calcium phosphate has been disclosed (for example, see Patent Document 6 and other references).

A makeup cosmetic that uses pearlescent scaly glass coated with a coating containing amorphous calcium phosphate (ACP, $Ca_3(PO_4)_2 \cdot nH_2O$) (amorphous calcium phosphate-coated particles) has been disclosed. The amorphous calcium phosphate content relative to the total mass of the amorphous calcium phosphate-coated particles is from 1 mass % to less than 10 mass % (for example, see Patent Document 7 and other references).

Patent Document 1: DE 2429762
Patent Document 2: U.S. Pat. No. 4,084,983
Patent Document 3: JP 2001-234090 A
Patent Document 4: JP 2003-213156 A
Patent Document 5: JP 2001-89324 A
Patent Document 6: JP 2007-217495 A
Patent Document 7: JP 2007-217319 A

SUMMARY OF INVENTION

Technical Problem

In connection with the prior-art bright pigments described in Patent Documents 1 to 5, cosmetic compositions containing such pigments are not satisfactory in spreadability, feel upon application and biocompatibility due to their poor oil adsorbability when applied to the outer skin (the horny layer) and the surface of a keratinous material, a type of protein, such as nail or hair.

Although amorphous calcium phosphate (ACP, $Ca_3(PO_4)_2 \cdot nH_2O$) has high oil adsorbability and superior acidic material (acidic dye) adsorbability, it is highly soluble in water and sweat and is problematic in being unstable as a coating.

Moreover, not only basic skin-care products but also makeup cosmetic compositions have recently been required to retain moisture, protect the skin, and have a skin structure-activating property, which are deeply associated with an anti skin-aging effect and a skin beautifying effect, as well as have an improved feel and resistance to makeup deterioration.

Accordingly, the present invention provides a bright pigment that has enhanced oil adsorbability and a cosmetic composition that has good spreadability over, and a good feel upon application to, the outer skin and the surface of a keratinous material, that has high biocompatibility and that is resistant to makeup deterioration.

Solution to Problem

The bright pigment of the present invention contains a scaly substrate and an outermost coating that covers the scaly substrate, that is provided as the outermost layer and that contains at least one member selected from the group consisting of hydroxyapatite and hydrocalumite.

The cosmetic composition of the present invention contains the bright pigment of the present invention.

A preferable example of the bright pigment of the present invention further is provided with an interference color coating that covers the scaly substrate, that is disposed more towards the center than the outermost coating and that contains at least one metal oxide selected from the group consisting of titanium oxide and iron oxide.

A preferable example of the bright pigment of the present invention further is provided with a silver-containing coating that covers the scaly substrate, that is disposed more towards the center than the outermost coating and that contains silver and/or a silver alloy.

In a preferable example of the bright pigment of the present invention, the outermost coating contains an anionic pigment.

In a preferable example of the bright pigment of the present invention, the thickness of the outermost coating is 10 nm to 100 nm.

In a preferable example of the bright pigment of the present invention, the thickness of the interference color coating is 20 nm to 300 nm.

In a preferable example of the bright pigment of the present invention, the thickness of the silver-containing coating is 20 nm to 100 nm.

In a preferable example of the bright pigment of the present invention, the silver-containing coating contains at least one member selected from the group consisting of a silver-gold alloy, a silver-palladium alloy, a silver-platinum alloy, a silver-copper alloy, a silver-gold-palladium alloy, a silver-platinum-palladium alloy, a silver-copper-palladium alloy, a silver gold-copper alloy and a silver gold-platinum alloy.

In a preferable example of the bright pigment of the present invention, the average particle diameter of the scaly substrate is 10 to 500 μm, and the average thickness thereof is 0.3 to 10 μm.

An example of the cosmetic composition of the present invention contains a medium and at least one member selected from the group consisting of collagen and hyaluronic acid.

EMBODIMENT 1

In Embodiment 1, an example of the bright pigment of the present invention is described.

Figure 1:
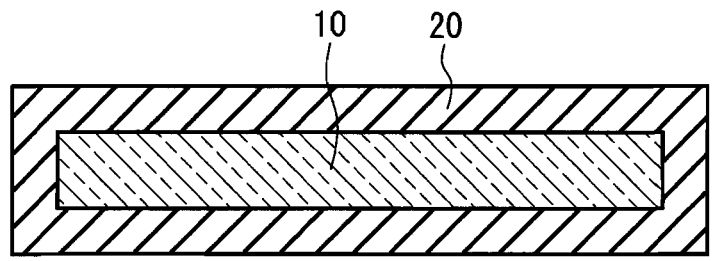
FIG. 1 is a cross-sectional view of an example of the bright pigment of the present invention.
Figure 2:
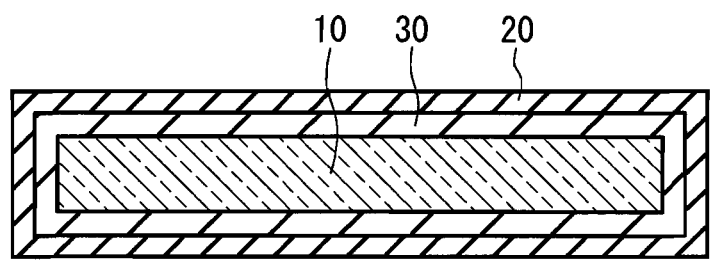
FIG. 2 is a cross-sectional view of another example of the bright pigment of the present invention.
Figure 3:
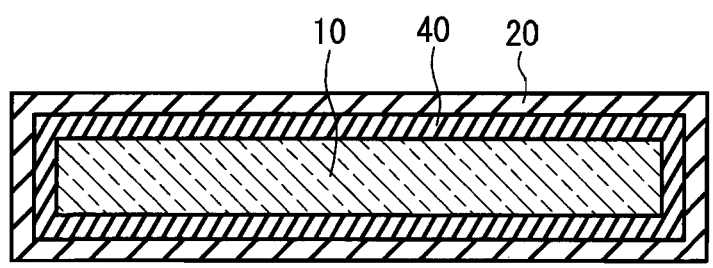
FIG. 3 is a cross-sectional view of another example of the bright pigment of the present invention.

As shown in FIG. 1, an example of the bright pigment of the present invention is composed of a scaly substrate (for example, a scaly glass substrate) 10 and an outermost coating 20 containing at least one member selected from the group consisting of hydroxyapatite and hydrocalumite. Furthermore, as shown in FIG. 2, in another example of the bright pigment of the present invention, the scaly substrate 10 is coated with an interference color coating 30 and the outermost coating 20 in this order. As shown in FIG. 3, in still another example of the bright pigment of the present invention, the scaly substrate 10 is coated with a silver-containing coating 40 and the outermost coating 20 in this order.

Scaly Substrate

Examples of the material of the scaly substrate 10 include at least one member selected from the group consisting of glass, natural mica, synthetic mica, silica and alumina. Among these materials, glass is preferable because it is easy to obtain a smooth surface.

The average particle diameter of the scaly substrate 10 is selected suitably according to the type and other factors of the cosmetic composition, and is usually preferably 10 μm to 500 μm, and more preferably 20 μm to 250 μm. When the average particle diameter is 10 μm to 500 μm, each particle shines intensely and a cosmetic composition having more glitter and a particle-like tone can be attained.

The average thickness of the scaly substrate 10 is preferably 0.3 μm to 10 μm, and more preferably 0.7 μm to 3 μm. The average thickness of 0.3 μm to 10 μm is preferable because the spreadability and the feel upon application of a cosmetic composition containing the bright pigment of the present invention to the surface of keratin, which constitutes horny structures such as skin, nails, lips, etc., are good.

A method for producing the scaly substrate 10 is not particularly limited, and a blowing method is preferable when the scaly substrate 10 is, for example, a scaly glass substrate. In a blowing method, a starting-material cullet is melted first. Molten glass is discharged continuously from a circular slit, and simultaneously a gas, such as air, is blown in from a blow nozzle provided inside the circular slit. Thereby, the molten glass is inflated and expanded into the shape of a balloon. By pulverizing the balloon-shaped glass, a scaly glass substrate can be obtained.

Interference Color Coating

The interference color coating contains at least one metal oxide selected from the group consisting of titanium oxide and iron oxide. The scaly substrate 10 gives brightness when it is coated with an interference color coating containing these ingredients. The interference color coating may have a single-layer structure whose layer contains at least one metal oxide selected from the group consisting of titanium oxide and iron oxide, or may have a multiple-layer structured. It is preferable that the interference color coating is composed of at least one metal oxide selected from the group consisting of titanium oxide and iron oxide. When the interference color coating has multiple layers, it is preferable that each layer is composed of at least one metal oxide selected from the group consisting of titanium oxide and iron oxide.

Titanium dioxide has 3 crystal forms, i.e., anatase, brookite and rutile. Among these, the anatase type and the rutile type are manufactured industrially. Anatase-type titanium dioxide has a strong photocatalytic activity and thus accelerates the decomposition and discoloration of resin or the like. On the other hand, rutile-type titanium dioxide has a weaker photocatalytic activity than anatase-type titanium dioxide by a factor of about 10 and is therefore suitable as a pigment to be contained in a cosmetic composition. Moreover, since the use of rutile-type titanium dioxide enables a coating that has a high refractive index, that is dense and that is uniform to be formed, this results in better color development by light interference.

As with rutile-type titanium dioxide, iron oxide has a weaker photocatalytic activity than anatase-type titanium dioxide by a factor of about 10 and is therefore suitable as a pigment to be contained in a cosmetic composition. Thus, the use of iron oxide as a pigment of an interference color coating allows a color that is created by the combination of chromatic color development caused by the light absorption of the iron oxide and color development caused by light interference to be attained.

An example of a method for forming a coating that contains rutile-type titanium dioxide is precipitating rutile-type titanium dioxide on the surface of an object to be coated by initiating a neutralization reaction in a titanium-containing solution that contains the object to be coated and has a temperature of 55 to 85° C. and a pH of 1.3 or less (for example, see JP2001-31421 A). With this method, a rutile-type titanium dioxide coating can also be fixed readily to the surface of a substrate that has poor heat resistance.

An example of a method for forming a coating that contains iron oxide is precipitating iron oxide on the surface of an object to be coated by initiating a neutralization reaction in an iron-containing solution that contains the object to be coated and has a temperature of 50 to 80° C. and a pH of 2 to 4 (for example, see JP 2005-187782 A).

It is preferable that the thickness of the interference color coating is 20 nm to 300 nm.

Examples of commercially available scaly glass substrates coated with a rutile-type titanium dioxide coating include the METASHINE (registered trade name) RC series (MC5090RS, MC5090RY, MC5090RR, MC5090RB, MC5090RG, MC1080RS, MC1080RY, MC1080RR, MC1080RB, MC1080RG, MC1040RS, MC1040RY, MC1040RR, MC1040RB, MC1040RG, MC1030RS, MC1030RY, MC1030RR, MC1030RB, MC1030RG, MC1020RS, MC1020RY, MC1020RR, MC1020RB, MC1020RG), which is marketed by the present applicant.

Examples of commercially available scaly glass substrates coated with an iron oxide coating include the METASHINE (registered trade name) TC series (MC5090TY, MC5090TZ, MC5090TP, MC5090TA, MC1080TY, MC1080TZ, MC1080TP, MC1080TA, MC1040TY, MC1040TZ, MC1040TP, MC1040TA, MC1030TY, MC1030TZ, MC1030TP, MC1030TA, MC1020TY, MC1020TZ, MC1020TP, MC1020TA), which is marketed by the present applicant.

Examples of commercially available scaly glass substrates coated with a rutile-type titanium dioxide coating and an iron oxide coating in this order include MC5090TY, MC1080TY, MC1040TY, MC1030TY, MC1020TY, which are marketed by the present applicant.

Silver-Containing Coating

The silver-containing coating 40 contains elemental silver and/or a silver-based alloy. When the silver-containing coating 40 contains elemental silver, the silver-containing coating 40 may consist essentially of silver. When the silver-containing coating 40 contains a silver-based alloy, the silver-containing coating 40 may consist essentially of a silver-based alloy.

When the total mass of the bright pigment of the present invention is 100 mass %, silver (including the silver in a silver-based alloy) is contained preferably in a proportion of 10 mass % or more, more preferably 15 mass % or more, and further more preferably 20 to 25 mass % or more, from the view point of securing a high brightness.

Examples of silver alloys include a silver-gold alloy, a silver-palladium alloy, a silver-platinum alloy, a silver-copper alloy, a silver gold-palladium alloy, a silver-platinum-palladium alloy, a silver-copper-palladium alloy, a silver-gold-copper alloy and a silver-gold-platinum alloy. Silver alloys are preferable in that they have higher water resistance and corrosion resistance than elemental silver.

A method for coating the inorganic substrate 10 with the silver-containing coating 40 is not particularly limited, and a known coating forming method can be used.

Examples of commercially available scaly glass substrates coated with elemental silver include the METASHINE (registered trade name) PS series (MC2080PS, MC5480PS, MC5230PS, MC5150PS, MC5090PS, MC5030PS, ME2040PS, ME2025PS), which is marketed by the present applicant.

The thickness of the silver containing coating is preferably 20 to 100 nm. With the coating thickness being 20 to 100 nm, the cost of providing a silver-containing coating can be kept from being high and the amount of light being reflected can be effectively increased, and it is thus possible to enhance the brightness of the bright pigment.

A method for forming a silver-containing coating is not particularly limited, and examples include sputtering, CVD, electroless (chemical) plating, and like methods. In particular, electroless plating is preferable in that a uniform coating can be formed readily over the scaly substrate.

In an electroless plating solution, examples of metallic ingredients include the following compounds:

(1) a silver-containing ingredient: silver nitrate,
(2) gold-containing ingredients: sodium aurous sulphite, chloroaurate(III) (tetrachloroaurate(III) tetrahydrate),
(3) palladium-containing ingredients: diamino palladium nitrite, palladium(II) chloride, palladium(II) nitrate, tetraammine palladium(II) dichloride,
(4) platinum-containing ingredients: chloroplatinic(IV) acid (hexachloroplatinic(IV) acid hexahydrate), dinitrodiammineplatinum(II), tetraamminedichloroplatinum(II), and
(5) copper-containing ingredients: copper nitrate, copper chloride, copper sulfate, copper acetate.

It is preferable to avoid the use of cyanide compounds from the viewpoint of safety.

Outermost Coating

The outermost coating contains at least one member selected from the group consisting of hydroxyapatite and hydrocalumite.

The thickness of the outermost coating is preferably 10 nm to 100 nm because its collagen and hyaluronic acid absorbability, oil-supplying properties, coloring properties due to pigment inclusion, and other properties are enhanced.

A hydroxyapatite coating can be formed according to, for example, the following method.

Hydroxyapatite ($Ca_{10}(PO_4)_6(OH)_2$) generally can be obtained by mixing a calcium salt solution and a phosphate solution.

Examples of calcium salts for use in the synthesis of hydroxyapatite include calcium hydroxide, calcium acetate, calcium carbonate, calcium chloride, calcium citrate, calcium lactate and like calcium salts. Examples of phosphates include ammonium phosphate, sodium phosphate, potassium phosphate, pyrophosphate, sodium hexametaphosphate and like phosphates.

The amounts of calcium salt and phosphate to be reacted are suitably such that the Ca/P ratio (molar ratio) is 1.4 to 1.8.

A suspension containing an aforementioned calcium source and phosphate source as well as a target to be coated with the outermost coating (such as a scaly substrate, a scaly substrate coated with an interference color coating, a scaly substrate coated with a silver-containing coating, or a scaly substrate coated with an interference color coating and a silver-containing coating) is neutralized with an alkali, and hydroxyapatite thus can be deposited on the surface of the target to be coated, and in this manner it is possible to form a coating of hydroxyapatite.

If an anionic pigment is added to the suspension, the target to be coated is coated with a hydroxyapatite coating in which the anionic pigment is dispersed. The anionic pigment having penetrated into the fine pores of hydroxyapatite forms a coordination bond with the calcium site of the hydroxyapatite; therefore, the coating of hydroxyapatite is colored.

It is preferable that the average particle diameter of the primary particles of the hydroxyapatite particles is controlled so as to be 50 nm or less by adjusting the temperature of the suspension during the neutralization reaction to 10° C. to 40° C.

Hydrocalumite is a layered crystalline compound that takes the form of a divalent or trivalent metal composite hydroxide and has anion exchangeability.

The composition of hydrocalumite is represented by the following formula (oxide form):

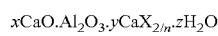

$$x CaO \cdot Al_2O_3 \cdot y CaX_{2/n} \cdot z H_2O$$

(where x, y and z represent a number within the ranges of 2=x=5, 0=y=4 and 0=z=30, respectively; X is a univalent or divalent acidic dye; and n indicates a valence of 1 or 2).

A hydrocalumite coating can be formed according to, for example, the following method.

A source of calcium divalent metal ions, a source of aluminium trivalent metal ions and a target to be coated are added to water to prepare a suspension. This suspension is neutralized with, for example, an alkali. Then, the target to be coated is coated with hydrocalumite.

If an anionic pigment is added to the suspension, in addition to the target to be coated being coated with hydrocalumite, the anionic pigment is intercalated between the layers of the crystalline structure of the hydrocalumite. The intercalated anionic pigment forms a coordination bond with the calcium site of the hydrocalumite; therefore, the coating of hydrocalumite is colored.

Calcium ion sources include lime milk slurry, water-soluble calcium salts, and the like. Aluminium sources include aluminates, inorganic acids, water-soluble salts thereof, organic acids, water-soluble salts thereof, and the like. Alkalis include sodium hydroxide, potassium hydroxide, ammonia, and the like.

Anionic pigments include soluble anionic pigments among the tar pigments for use in food products specified by the Japanese Food Sanitation Act and pharmaceuticals, quasi-medical products and cosmetics specified by the Japanese Pharmaceutical Affairs Act. The color of the anionic pigments is not particularly limited. For example, the following pigments can be mentioned. Anionic pigments are pigments that have an acidic group such as a sulfone group, a carboxyl group or a phosphoric acid group.

Examples of yellow pigments include Acid Yellow 23 defined by the Color Index Generic Name (C.I.G.N) (Japanese official color code: Yellow No. 4. Parenthetical color codes provided below are also of the Japanese official color codes.) Food Yellow 3 (Yellow No. 5), Acid Yellow 73 (Yellow No. 202(1), Yellow No. 202(2)), Acid Yellow 3 (Yellow No. 203), Acid Yellow 40 (Yellow No. 402), Acid Yellow 1 (Yellow No. 403), Acid Yellow 36 (Yellow No. 406), Acid Yellow 11 (Yellow No. 407), and the like.

Examples of blue pigments include Blue No. 1, Blue No. 2, Blue No. 202, Blue No. 203, Blue No. 205, and the like.

Examples of red pigments include Red No. 2, Red No. 3, Red No. 102, Red No. 104(1), Red No. 105(1), Red No. 106, Red No. 201, Red No. 202, Red No. 227, Red No. 230(1), Red No. 230(2), Red No. 231, Red No. 232, Red No. 401, Red No. 502, Red No. 503, Red No. 504, Red No. 506, and the like.

Examples of green pigments include Green No. 3, Green No. 201, Green No. 204, Green No. 205, Green No. 401, Green No. 402, and the like.

Examples of orange pigments include Orange No. 205, Orange No. 207, Orange No. 402, and the like.

An example of a brown pigment is Brown No. 201 and the like.

An example of a purple pigment is Purple No. 401 and the like.

An example of a black pigment is Black No. 401 and the like.

When an anionic pigment is contained in the outermost coating, it is preferable that at least one member selected from the group consisting of a hydroxide of cerium, an oxide hydrate of cerium, a hydroxide of aluminium and an oxide hydrate of aluminium is contained in the outermost coating to enhance the lightfastness of the anionic pigment. Although titanium dioxide and iron oxide that are contained in the interference color coating have a photocatalytic function and absorb ultraviolet rays, if at least one member selected from the group consisting of a hydroxide of cerium, an oxide hydrate of cerium, a hydroxide of aluminium and an oxide hydrate of aluminium is contained in the outermost coating, the oxidative decomposition of the anionic pigment by the titanium dioxide or iron oxide is inhibited. Although silver and/or a silver alloy that are contained in the silver-containing coating also exhibit a catalytic action by which the anionic pigment is oxidatively decomposed, if at least one member selected from the group consisting of a hydroxide of cerium and oxide hydrate of cerium is contained in the outermost coating, the oxidative decomposition of the anionic pigment by the silver and/or silver alloy is inhibited.

Hydroxide of Cerium or a Oxide Hydrate of Cerium

Hydroxide of cerium or oxide hydrate of cerium can be precipitated on particles (for example, a scaly substrate coated with an interference color coating, a scaly substrate coated with a silver-containing coating, or a scaly substrate coated with an interference color coating and a silver-containing coating) by reacting a water-soluble cerium compound with an acid or an alkali.

Water-soluble cerium compounds include acidic cerium compounds, in particular, mineral acid salts such as cerium sulfate, cerium chloride and cerium nitrate. By reaction with an alkali such as an alkali metal hydroxide, an acidic cerium compound enables hydroxide of cerium or oxide hydrate of cerium to be precipitated. Moreover, water-soluble cerium compounds include, in addition to acidic cerium compounds, alkaline cerium salts such as cerium ammonium sulfate or cerium ammonium nitrate, which allow hydroxide of cerium or oxide hydrate of cerium to be precipitated via a reaction with an acid, for example, sulfuric acid. It is preferable that cerium nitrate is used as a water-soluble cerium compound and a sodium hydroxide solution is used as an alkali for reaction therewith. When the total mass of the at least one member selected from the group consisting of titanium dioxide, iron oxide, silver and a silver alloy contained in the bright pigment is 100, a water-soluble cerium compound preferably is contained in the bright pigment in a proportion of 0.01 to 1.0 based on cerium. Furthermore, when the total mass of the at least one member selected from the group consisting of titanium dioxide, iron oxide, silver and a silver alloy contained in the bright pigment is 100, it is more preferable that a water-soluble cerium compound is added to an aqueous slurry containing at least one member selected from the group consisting of hydroxyapatite and hydrocalumite such that the water-soluble cerium compound is contained in the bright pigment in a proportion of 0.02 to 0.5 based on cerium. The amount of alkali or acid contained in the aqueous slurry is not particularly limited insofar as it is sufficient to cause hydroxide of cerium or oxide hydrate of cerium to precipitate on the target to be coated with the outermost coating (such as a scaly substrate coated with an interference color coating, a scaly substrate coated with a silver-containing coating, or a scaly substrate coated with an interference color coating and a silver-containing coating).

Hydroxide of Aluminium or Oxide Hydrate of Aluminium

Hydroxide of aluminium or oxide hydrate of aluminium can be obtained by reacting an acidic or alkaline aluminium compound with a suitable alkali or acid and, simultaneously with this reaction, can be precipitated on particles (for example, a scaly substrate coated with an interference color coating, a scaly substrate coated with a silver-containing coating, or a scaly substrate coated with an interference color coating and a silver-containing coating).

Examples of acidic aluminium compounds include aluminium salts of mineral acids, such as aluminium chloride, aluminium sulfate and aluminium nitrate. Examples of alkaline aluminium compounds include alkali metal aluminates such as sodium aluminate. It is preferable that, when the total mass of the at least one metal oxide selected from the group consisting of titanium oxide and iron oxide contained in the interference color coating is 100, the acidic or alkaline aluminium compound is contained in a proportion of 2 to 4 based on aluminium. Furthermore, when the total mass of the metal oxide contained in the interference color coating is 100, it is more preferable that the aluminium compound is added to an aqueous slurry containing at least one member selected from the group consisting of hydroxyapatite and hydrocalumite such that the aluminium compound is contained in the bright pigment in a proportion of 2.5 to 3.5 based on aluminium. The amount of alkali or acid contained in the aqueous slurry is not particularly limited insofar as it is sufficient to cause hydroxide of aluminium or oxide hydrate of aluminium to precipitate on the target to be coated with the outermost coating (such as a scaly substrate coated with an interference color coating, a scaly substrate coated with a silver-containing coating, or a scaly substrate coated with an interference color coating and a silver-containing coating).

EMBODIMENT 2

In Embodiment 2, an example of the cosmetic composition of the present invention is described.

An example of the cosmetic composition of the present invention contains at least one member selected from the group consisting of collagen and hyaluronic acid, the bright pigment of embodiment 1, and a medium. The cosmetic composition of the present invention may not necessarily contain the at least one member selected from the group consisting of collagen and hyaluronic acid or a medium, and may be composed solely of the bright pigment of the present invention.

Collagen is positively charged due to the amino group thereof and is cationic. On the other hand, hyaluronic acid is negatively charged due to the carboxyl group thereof and is anionic. Therefore, when hyaluronic acid and collagen are mixed in a simple manner, the carboxyl group (negatively charged) of the hyaluronic acid and the amino group (positively charged) of the collagen are bonded and create a precipitate called a polyion complex and, due to the presence of this precipitate, the uniformity of the cosmetic composition is impaired.

Since an example of the bright pigment of the present invention is added to the cosmetic composition of the present invention, the bonding of collagen and hyaluronic acid can be inhibited by the at least one member selected from the group consisting of hydroxyapatite and hydrocalumite contained in the outermost coating that constitutes the bright pigment, and it is thus possible to inhibit the development of polyion complex precipitation.

More specifically, for example, when a bright pigment having an outermost coating containing hydroxyapatite as well as collagen and hyaluronic acid are added to a medium, the development of polyion complex precipitation is inhibited because cationic collagen is adsorbed onto the phosphate site and anionic hyaluronic acid is adsorbed onto the calcium site of the hydroxyapatite.

For example, when a bright pigment having an outermost coating containing hydrocalumite as well as collagen and hyaluronic acid are added to a medium, the development of polyion complex precipitation is inhibited because anionic hyaluronic acid is adsorbed onto the calcium site of the hydrocalumite.

Examples of the medium contained in the cosmetic composition of the present invention may be different according to the type of the cosmetic composition, and include ketones that are liquid at room temperature, such as methyl ethyl ketone, methyl isobutyl ketone, diisobutyl ketone, isophorone, cyclohexanone and acetone; alcohols that are liquid at room temperature, such as ethanol, isopropanol, diacetone alcohol, 2-butoxyethanol and cyclohexanol; glycols that are liquid at room temperature, such as ethylene glycol, propylene glycol, pentylene glycol and glycerol; propylene glycol ethers that are liquid at room temperature, such as propylene glycol monomethyl ether, propylene glycol monomethyl ether acetate and dipropylene glycol mono-n-butyl ether; short-chain esters (containing 3 to 8 carbon atoms in total) such as ethyl acetate, methyl acetate, propyl acetate, n-butyl acetate and isopentyl acetate; alkanes that are liquid at room temperature, such as decane, heptane, dodecane and cyclohexane; cyclic aromatic compounds that are liquid at room temperature, such as toluene and xylene; and the like. In particular, alcohols and short-chain esters are preferable from the view point of safety.

The cosmetic composition of the present invention further may contain, as necessary, a moisturizing agent, a solid oil, a liquid oil, a powder or the like other than hyaluronic acid and collagen insofar as the inhibiting effect on the development of polyion complex precipitation is not impaired.

Examples of moisturizing agents include polyethylene glycol, propylene glycol, glycerol, 1,3-butylene glycol, hexylene glycol, xylitol, sorbitol, maltitol, chondroitin sulfate, mucoitinsulfuric acid, caronic acid, atelocollagen, cholesteryl-12-hydroxystearate, sodium lactate, bile salt, dl-pyrrolidonecarboxylate, diglycerol (EO) PO adduct, chestnut rose (*Rosa roxburghii*) extract, yarrow (*Achillea millefolium*) extract, melilot (*Melilotus officinalis*) extract, and the like. Two or more of such moisturizing components may be used in combination.

Examples of solid oils include hydrocarbons such as polyethylene wax, ethylene propylene copolymer, solid paraffin wax, ceresin wax, microcrystalline wax, Fischer-Tropsch wax or montan wax; waxes such as carnauba wax, candelilla wax, bees wax, Japan wax or spermaceti wax; oils and fats such as cacao butter, palm oil or beef tallow; higher fatty acids such as stearic acid, lauric acid, myristic acid or behenic acid; higher alcohols such as cetyl alcohol, stearyl alcohol, lauryl alcohol or behenyl alcohol; hydrogenated oils such as hydrogenated coconut oil or hydrogenated castor oil; esters such as methyl stearate, cetyl palmitate, pentaerythritol rosinate or propylene glycol distearate; silicone waxes such as stearyl-modified polysiloxane or behenyl-modified polysiloxane; and the like. Two or more of such solid oils may be used in combination.

Liquid oils, regardless of their source, i.e., animal oil, vegetable oil or synthetic oil, include hydrocarbons, oils and fats, hydrogenated oils, ester oils, aliphatic acids, higher alcohols, silicone oils, fluorine-based oils, lanolin derivatives, oil-based gelling agents, lipophilic surfactants, oil-soluble ultraviolet absorbers, and the like. Specifically, hydrocarbons such as liquid paraffin, squalane, Vaseline, polyisobutylene or polybutene; oils and fats such as olive oil, castor oil, jojoba oil, mink oil or macadamia nut oil; esters such as cetyl isooctanate, isopropyl myristate, isopropyl palmitate, octyldodecyl myristate, glyceryl trioctanate, diglyceryl diisostearate, diglyceryl triisostearate, glyceryl tribehenate, pentaerythritol rosinate, neopentyl glycol dioctanate, cholesterol fatty acid ester or di(cholesteryl-behenyl-octyldodecyl) N-lauroyl-L-glutamate; aliphatic acids such as isostearic acid or oleic acid; higher alcohols such as oleyl alcohol or isostearyl alcohol; silicones such as dimethyl polysiloxane of a low degree of polymerization, dimethyl polysiloxane of a high degree of polymerization, methylphenyl polysiloxane, decamethylcyclopentasiloxane, octamethylcyclotetrasiloxane, polyether-modified polysiloxane, crosslinked organopolysiloxane or fluorine-modified silicone; fluorine-based oil solutions such as perfluoropolyether, perfluorodecane or perfluorooctane; lanolin derivatives such as lanolin acetate, lanolin fatty acid isopropyl ester or lanolin alcohol; oil-based gelling agents such as dextrin fatty acid ester, sucrose fatty acid ester, starch fatty acid ester, aluminium 12-hydroxystearate or calcium stearate; oil-soluble ultraviolet absorbers such as ethyl p-aminobenzoate, p-methoxycinnamic acid-2-ethylhexyl, 4-tert-butyl-4'-methoxydibenzoylmethane or oxybenzone; and the like are included. Two or more of such liquid oils may be used in combination.

The shape of powders is not particularly limited and may take any spherical, plate-like or needle-like form. Also, the particle size thereof may be smaller than that of the bright pigment of the present invention, or may be the same as that of the bright pigment of the present invention. Moreover, the structure thereof may be either porous or nonporous.

Examples of the powders include inorganic powders, bright powders, organic powders, pigmentary powders or composite powders. Two or more such powders may be used in combination, and such powders may be surface-treated with metal oxide, metal hydroxide, a fluorine compound, a silicone-based oil, a metallic soap, a wax, a fatty oil or fat, a hydrocarbon, or the like.

Examples of inorganic powders include titanium oxide powder, black titanium oxide powder, ferric ammonium ferrocyanide powder, lazurite powder, red iron oxide powder, yellow iron oxide powder, black iron oxide powder, zinc oxide powder, aluminium oxide powder, magnesium oxide powder, zirconium oxide powder, magnesium carbonate powder, calcium carbonate powder, chromium oxide powder, chromium hydroxide powder, carbon black powder, aluminium silicate powder, magnesium silicate powder, aluminium magnesium silicate powder, mica powder, synthetic mica powder, synthetic sericite powder, sericite powder, talc powder, kaolin powder, silicic anhydride powder, silica bead powder, silicon carbide powder, barium sulfate powder, bentonite powder, smectite powder, boron nitride powder, or the like.

Examples of bright powders include bismuth oxychloride powder, titanium natural mica powder, iron oxide-coated natural mica powder, iron oxide titanium natural mica powder, organic pigment-treated titanium natural mica powder, aluminium powder, or the like.

Examples of organic powders include nylon powder, polymethylmethacrylate, acrylonitrile-methacrylic acid copolymer powder, vinylidene chloride-methacrylic acid copolymer powder, polystyrene powder, polymethylsilsesquioxane powder, organopolysiloxane elastomer powder, urethane powder, wool powder, silk powder, crystalline cellulose, N-acyl lysine, or the like.

Examples of pigmentary powders include organic tar-based pigments, lake pigments of organic dyes, or the like.

Examples of composite powders include reduced titanium natural mica powder coated with fine titanium oxide particles, titanium natural mica powder coated with fine zinc oxide particles, titanium natural mica powder coated with barium sulfate, titanium oxide-containing silicon dioxide powder, zinc oxide-containing silicon dioxide powder, or the like.

The cosmetic composition of the present invention further may contain a surfactant, an antioxidant, an aroma chemical, a preservative, water, a polyhydric alcohol such as glycerol or 1,3-butylene glycol, a lower alcohol, a beauty component, or the like as necessary.

The cosmetic composition of the present invention can be obtained by mixing by known means at least one member selected from the group consisting of collagen and hyaluronic acid, the bright pigment of the present invention and a medium.

The type of the cosmetic composition of the present invention is not particularly limited, and examples include nail cosmetics such as nail colors or nail coatings; eyebrow and eye cosmetics such as eye shadows, eyeliners, mascaras or eyebrow colors; pencil-shaped makeup cosmetics such as eyeliner pencils or lipliner pencils; makeup cosmetics such as foundations, blushes, face colors, lipsticks or lip glosses; makeup cosmetics of a sedimentation type that contain a glittering agent as a sediment in water or a solvent and that are shaken appropriately before use; or the like.

Next, preferable amounts of the bright pigment of the present invention in the cosmetic composition will be described according to the type of the cosmetic composition.

For nail cosmetics such as nail colors, the amount of the bright pigment of the present invention is, from the viewpoint of balancing high brightness and good applicability, preferably 0.1 to 50 mass % and more preferably 3 to 40 mass % when the total mass of the cosmetic composition is 100 mass %. In this case, it is preferable that the average particle diameter of the bright pigment of the present invention is 20 to 500 μm and the average thickness is 1 to 10 μm.

For solid cosmetic powders such as eye shadows or blushes that are obtained by dry-filling with a powder using a press, or wet-filling with a powder using a volatile solvent and then drying it, the amount of the bright pigment of the present invention is, from the viewpoint of balancing high brightness and a good skin feel upon application, preferably 5 to 80% and more preferably 10 to 60%. In this case, it is preferable that the average particle diameter of the bright pigment of the present invention is 10 to 250 μm and the average thickness is 0.3 to 3 μm.

For powdered cosmetics such as eye shadows or face colors that are used as loose powder, the amount is preferably 70 to 100% because they come into contact with human fat present on the skin upon application. In this case, it is preferable that the average particle diameter of the bright pigment of the present invention is 10 to 250 μm and the average thickness is 0.3 to 3 μm.

For oil-based solid cosmetics such as lip glosses, lipsticks or oil-based eye shadows, the amount of the bright pigment of the present invention is preferably 1 to 60 mass % and more preferably 3 to 50 mass % from the viewpoint of sufficiently exerting the effect of the bright pigment of the present invention as a glittering agent and securing good moldability. In this case, it is preferable that the average particle diameter of the bright pigment of the present invention is 10 to 250 μm and the average thickness is 0.3 to 3 μm.

For emulsion-type makeup cosmetics obtained by emulsifying an aqueous phase and an oil phase with an activator, the amount of the bright pigment of the present invention is preferably 1 to 50 mass % and more preferably 3 to 40 mass % from the viewpoint of sufficiently exerting the effect of the bright pigment of the present invention as a glittering agent and securing high emulsification stability. In this case, it is preferable that the average particle diameter of the bright pigment of the present invention is 10 to 250 μm and the average thickness is 0.3 to 3 μm.

For water-based makeup cosmetics such as water-based mascaras or water-based gels in which a water-soluble resin, a water-based resin emulsion, a thickener, or the like is mixed with water, the amount of the bright pigment of the present invention is preferably 0.1 to 60 mass % and more preferably 1 to 40 mass % from the viewpoint of sufficiently exerting the effect of the bright pigment of the present invention as a glittering agent and securing a good feel upon application. In this case, it is preferable that the average particle diameter of the bright pigment of the present invention is 10 to 250 μm and the average thickness is 0.3 to 3 μm.

EXAMPLES

Examples and comparative examples are given below to describe the present invention in more detail.

The various average particle diameters given below refer to the particle sizes at which the cumulative volume frequency is 50% when calculated from the smaller particle size side (median sizes (also generally referred to as D50)), and the volume-based particle size distribution was measured using a laser diffraction particle size analyzer.

The average thickness of a scaly glass substrate was obtained by measuring the thickness of 100 scaly substrate particles and taking an average. The thickness of each scaly substrate was obtained by measuring the optical path difference between direct light (light not affected by a phase object) and light transmitted through a scaly glass substrate using an interference microscope.

The average thickness of a bright pigment was obtained by measuring the thickness of 50 bright pigment particles and taking an average. The thickness of each bright pigment was measured using an image captured by an electron microscope. The average thickness of an intermediate product (for example, a scaly substrate coated with an interference color coating and a scaly substrate coated with a silver-containing coating) was measured in the same manner.

The thickness of each coating was measured according to secondary ion mass spectrometry (SIMS, a secondary ion-microprobe mass spectrometer manufactured by Cameca, IMS-6F). Specifically, the thickness of each coating was determined based on the component distribution from the surface of a bright pigment to the surface of a scaly substrate.

Example 1

The bright pigment of Example 1 is an extender pigment (average particle diameter: 41 μm, average thickness: 1.4 μm) having a structure in which a scaly substrate (scaly glass substrate) is coated with a hydroxyapatite coating. The bright pigment of Example 1 was produced in the following manner.

A scaly glass substrate having an average particle diameter of 40 μm and an average thickness of 1.3 μm was prepared as a scaly substrate. This scaly glass substrate was obtained by fabricating glass pieces according to a balloon method using molten glass as a starting material, pulverizing the glass pieces using a pulverizer, and sorting the glass pieces using a ultrasonic sieve.

Next, 30 g of the scaly glass substrate was added to 0.3 L of purified water to give a suspension and, while maintaining the temperature of the suspension at 30° C. in a water bath, an aqueous solution obtained in advance by dissolving 14 g of calcium acetate monohydrate in 60 ml of purified water and 5 ml of an aqueous phosphoric acid solution (phosphoric acid: 0.5 mol/L) were added dropwise to the suspension each over the period of 10 minutes. Thereafter, while the temperature of the suspension was maintained continually at 30° C., stirring was performed for 60 minutes.

Next, the suspension was filtered through filter paper and the filtered solids were removed, dried, and then subjected to a heat treatment performed in a furnace having a furnace atmosphere temperature of 120° C. for 2 hours. In this manner, the bright pigment of Example 1 in which a scaly glass substrate was coated with a hydroxyapatite coating (thickness: 50 nm) was obtained.

Example 2

The bright pigment of Example 2 is a pearlescent pigment (average particle diameter: 42 μm, average thickness: 1.6 μm) having a structure in which a scaly substrate (a scaly glass substrate, average particle diameter: 40 μm, average thickness: 1.3 μm) is coated with a titanium dioxide coating (thickness: 120 nm) and a hydroxyapatite coating (thickness: 50 nm) in this order. The bright pigment of Example 2 was produced in the following manner.

METASHINE (registered trade name) MC1040RR (manufactured by Nippon Sheet Glass Co., Ltd., pearlescent pigment) was used as a pigment. This has a structure in which a scaly glass substrate is coated with rutile-type titanium dioxide, has a lustrous red interference color, and has an average particle diameter of 40 μm and an average thickness of 1.5 μm.

A hydroxyapatite coating was formed over this pigment as in the case of the bright pigment of Example 1. The bright pigment of Example 2 thus obtained had a lustrous red interference color.

Example 3

The bright pigment of Example 3 is a pigment with a metallic luster (average particle diameter: 86 μm, average thickness: 1.5 μm) having a structure in which a scaly substrate (a scaly glass substrate, average particle diameter: 80 μm, average thickness: 1.3 μm) is coated with a silver-containing coating composed of silver and a hydroxyapatite coating (thickness: 50 nm) in this order. The bright pigment of Example 3 was produced in the following manner.

METASHINE (registered trade name) MC2080PS (manufactured by Nippon Sheet Glass Co., Ltd.) was used as a pigment in which a glass substrate was coated with a silver-containing coating. The silver-containing coating was formed according to an electroless plating method, and the thickness of the silver-containing coating was 40 nm. This pigment had a silver-gray metallic luster and had an average particle diameter of 80 μm and an average thickness of 1.4 μm.

A hydroxyapatite coating was formed over this pigment as in the case of the bright pigment of Example 1. The bright pigment of Example 3 thus obtained had a metallic luster.

Example 4

The bright pigment of Example 4 is a pearlescent pigment (average particle diameter: 42 μm, average thickness: 1.6 μm) having a structure in which a scaly substrate (a scaly glass substrate, average particle diameter: 40 μm, average thickness: 1.3 μm) is coated with a titanium dioxide coating (thickness: 100 nm) and an anionic dye-containing hydroxyapatite coating (thickness: 50 nm) in this order. The bright pigment of Example 4 was produced in the following manner.

METASHINE (registered trade name) MC1040RY (manufactured by Nippon Sheet Glass Co., Ltd., pearlescent pigment) was used as a pigment. This has a structure in which a scaly glass substrate is coated with rutile-type titanium dioxide, has a lustrous yellow interference color, and has an average particle diameter of 40 μm and an average thickness of 1.5 μm.

Next, 30 g of MC1040RY and 10 g (5 mass %) of an aqueous Red No. 202 solution were added to 0.3 L of purified water to give a suspension and, while maintaining the temperature of the suspension at 30° C. in a water bath, an aqueous solution obtained in advance by dissolving 14 g of calcium acetate monohydrate in 60 ml of purified water and 5 ml of an aqueous phosphoric acid solution (phosphoric acid: 0.5 mol/L) were added dropwise to the suspension each over the period of 10 minutes. Thereafter, while the temperature of the suspension was maintained continually at 30° C., stirring was performed for 60 minutes.

Next, the suspension was filtered through filter paper and the filtered solids were removed, dried, and then subjected to a heat treatment performed in a furnace having a furnace atmosphere temperature of 120° C. for 2 hours. In this manner, the bright pigment of Example 4 in which a scaly glass substrate was coated with a titanium dioxide coating and a red anionic dye-containing hydroxyapatite coating was obtained. The bright pigment of Example 4 had a pearlescence with a color created by the combination of the color of the red dye and an interference color.

Example 5

The bright pigment of Example 5 is a pearlescent pigment (average particle diameter: 43 μm, average thickness: 1.6 μm) having a structure in which a scaly substrate (a scaly glass substrate, average particle diameter: 40 μm, average thickness: 1.3 μm) is coated with a titanium dioxide coating (thickness: 100 nm) and an anionic dye-containing hydrocalumite coating (thickness: 50 nm) in this order. The bright pigment of Example 5 was produced in the following manner.

METASHINE (registered trade name) MC1040RY (manufactured by Nippon Sheet Glass Co., Ltd., pearlescent pigment) was used as a pigment. This has a structure in which a scaly glass substrate is coated with rutile-type titanium dioxide, has a lustrous yellow interference color, and has an average particle diameter of 40 μm and an average thickness of 1.5 μm.

Next, 30 g of MC1040RY and 10 g (5 mass %) of an aqueous Blue No. 1-containing solution were added to 0.3 L of purified water to give a suspension and, while maintaining the pH of the suspension at 6, an aqueous solution obtained in advance by dissolving 6 g of aluminium chloride hexahydrate and 14 g of calcium acetate monohydrate in 50 ml of purified water and an aqueous sodium hydroxide solution (10 mass %) were added dropwise each over the period of 10 minutes. Thereafter, while the pH and the temperature of the suspension were continually maintained at pH 6 and 90° C., respectively, stirring was performed for 30 minutes.

Next, the suspension was filtered through filter paper and the filtered solids were removed, dried, and then subjected to a heat treatment performed in a furnace having a furnace atmosphere temperature of 120° C. for 2 hours. In this manner, the bright pigment of Example 5 in which a scaly glass substrate was coated with a titanium dioxide coating and a blue anionic dye-containing hydrocalumite coating was obtained. The bright pigment of Example 5 had a pearlescence with a color created by the combination of the color of the blue dye and an interference color.

Example 6

The bright pigment of Example 6 is a pigment with metallic luster (average particle diameter: 85 μm, average thickness: 1.5 μm) having a structure in which a scaly substrate (a scaly glass substrate, average particle diameter: 80 μm, average thickness: 1.3 μm) is coated with a silver-containing coating composed of silver and an anionic dye-containing hydroxyapatite coating (thickness: 50 nm) in this order. The bright pigment of Example 6 was produced in the following manner.

METASHINE (registered trade name) MC2080PS (manufactured by Nippon Sheet Glass Co., Ltd.) was used as a pigment in which a scaly glass substrate was coated with a silver-containing coating. The silver-containing coating was formed according to an electroless plating method, and the thickness of the silver-containing coating was 40 nm. This pigment had a silver-gray metallic luster and had an average particle diameter of 80 μm and an average thickness of 1.4 μm.

Next, 30 g of the aforementioned "MC2080PS" and 10 g (10 mass %) of an aqueous Red No. 202-containing solution were added to 0.3 L of purified water to give a suspension and, while maintaining the temperature of the suspension at 30° C. in a water bath, an aqueous solution obtained in advance by dissolving 14 g of calcium acetate monohydrate in 60 ml of purified water and 5 ml of an aqueous phosphoric acid solution (phosphoric acid: 0.5 mol/L) were added dropwise each over the period of 10 minutes. Thereafter, while the temperature of the suspension was continually maintained at 30° C., stirring was performed for 60 minutes.

Next, the suspension was filtered through filter paper and the filtered solids were removed, dried, and then subjected to a heat treatment performed in a furnace having a furnace atmosphere temperature of 120° C. for 2 hours. In this manner, the bright pigment of Example 6 in which a scaly glass substrate was coated with a silver-containing coating and a red anionic pigment-containing hydroxyapatite coating was obtained. The bright pigment of Example 6 had a metallic luster casting a red light.

Example 7

The bright pigment of Example 7 is a pearlescent pigment (average particle diameter: 43 μm, average thickness: 1.6 μm) having a structure in which a scaly substrate (a scaly glass substrate, average particle diameter: 40 μm, average thickness: 1.3 μm) is coated with a titanium dioxide coating (thickness: 100 nm) and an anionic dye-containing hydroxyapatite coating (thickness: 50 nm) in this order. The bright pigment of Example 7 was produced in the following manner.

METASHINE (registered trade name) MC1040RY (manufactured by Nippon Sheet Glass Co., Ltd., pearlescent pigment) was used as a pigment. This has a structure in which a scaly glass substrate is coated with rutile-type titanium dioxide, has a lustrous yellow interference color, and has an average particle diameter of 40 μm and an average thickness of 1.5 μm.

Next, 30 g of MC1040RY and 10 g mass %) of an aqueous Red No. 202-containing solution were added to 0.3 L of purified water to give a suspension, and while maintaining the temperature of the suspension at 30° C. in a water bath, an aqueous solution obtained in advance by dissolving 14 g of calcium acetate monohydrate in 60 ml of purified water, 5 ml of an aqueous phosphoric acid solution (phosphoric acid: 0.5 mol/L) and an aqueous solution obtained by dissolving 0.4 g of diammonium cerium nitrate in 60 ml of purified water were added dropwise to the suspension each over the period of 10 minutes. Thereafter, while the temperature of the suspension was maintained continually at 30° C., stirring was performed for 60 minutes.

Next, the suspension was filtered through filter paper and the filtered solids were removed, dried, and then subjected to a heat treatment performed in a furnace having a furnace atmosphere temperature of 120° C. for 2 hours. In this manner, the bright pigment of Example 7 in which a scaly glass substrate was coated with a titanium dioxide coating and a red anionic dye-containing hydroxyapatite coating was obtained. The bright pigment of Example 7 had a pearlescence with a color created by the combination of the color of the red dye and an interference color.

Comparative Example 1

The bright pigment of Comparative Example 1 is the same as the bright pigment of Example 1 except that there is no hydroxyapatite coating provided. That is, the bright pigment of Comparative Example 1 is composed solely of a scaly glass substrate having an average particle diameter of 40 μm and an average thickness of 1.3 μm.

Comparative Example 2

The bright pigment of Comparative Example 2 is the same as the bright pigment of Example 2 except that there is no hydroxyapatite coating provided. That is, the bright pigment of Comparative Example 2 in which the scaly glass substrate is a METASHINE (registered trade name) MC1040RR (manufactured by Nippon Sheet Glass Co., Ltd., pearlescent pigment) coated with rutile-type titanium dioxide has a lustrous red interference color and has an average particle diameter of 40 μm and an average thickness of 1.5 μm.

Comparative Example 3

The bright pigment of Comparative Example 3 is the same as the bright pigment of Example 3 except that there is no hydroxyapatite coating provided. That is, in the bright pigment of Comparative Example 3, the scaly glass substrate is MC2080PS (manufactured by Nippon Sheet Glass Co., Ltd.) coated with a silver-containing coating. The silver-containing coating was formed according to an electroless plating method, and the thickness of the silver-containing coating was 40 nm. This pigment had a silver-gray metallic luster and had an average particle diameter of 80 μm and an average thickness of 1.4 μm.

Comparative Example 4

The bright pigment of Comparative Example 4 is a pearlescent pigment (average particle diameter: 43 μm, average thickness: 1.6 μm) having a structure in which a scaly substrate (a scaly glass substrate, average particle diameter: 40 μm, average thickness: 1.3 μm) is coated with a titanium dioxide coating (thickness: 100 nm) and an anionic dye-containing hydrotalcite coating (thickness: 50 nm) in this order. The bright pigment of Comparative Example 4 was produced in the following manner.

METASHINE (registered trade name) MC1040RY (manufactured by Nippon Sheet Glass Co., Ltd., pearlescent pigment) was used as a pigment. This has a structure in which a scaly glass substrate is coated with rutile-type titanium dioxide, has a lustrous yellow interference color, and the average particle diameter thereof is 40 μm and the average thickness thereof is 1.5 μm.

Next, a conditioning solution in which 3 g of aluminium chloride hexahydrate and 5 g of magnesium chloride hexahydrate were dissolved in 50 mL of purified water was prepared. Meanwhile, a suspension was obtained by adding 30 g of MC1040RY and 10 g (5 mass %) of an aqueous Red No. 202-containing solution to 0.3 L of purified water. While the temperature of the resulting suspension was maintained at 75° C. with a water bath, the entire quantity of the conditioning solution was added dropwise to the suspension over 10 minutes. The pH of the suspension was maintained at pH 6 using a 10 mass % aqueous sodium hydroxide solution during the dropwise addition of the conditioning solution. While the pH was continually maintained at pH 6, the suspension was stirred at 90° C. for 30 minutes.

Next, the suspension was filtered through filter paper and the filtered solids were removed, dried, and then subjected to heat treatment at 120° C. for 2 hours. In this manner, the bright pigment of Comparative Example 4 in which a scaly glass substrate was coated with a rutile-type titanium dioxide coating and an anionic red dye-containing hydrotalcite coating in this order was obtained. The bright pigment of Comparative Example 4 had a pearlescence with a color created by the combination of the color of the red anionic dye and a yellow interference color.

Comparative Example 5

The bright pigment of Comparative Example 5 is a pearlescent pigment (average particle diameter: 43 μm, average thickness: 1.6 μm) having a structure in which a scaly substrate (a scaly glass substrate, average particle diameter: 40 μm, average thickness: 1.3 μm) is coated with a titanium dioxide coating (thickness: 100 nm) and an anionic dye-containing aluminium hydroxide coating (thickness: 60 nm) in this order. The bright pigment of Comparative Example 5 was produced in the following manner.

METASHINE (registered trade name) MC1040RY (manufactured by Nippon Sheet Glass Co., Ltd., pearlescent pigment) was used as a pigment. This has a structure in which a scaly glass substrate is coated with rutile-type titanium dioxide, has an interference color with a yellow luster, and the average particle diameter thereof is 40 μm and the average thickness thereof is 1.5 μm.

Next, 30 g of MC1040RY was added to 0.3 L of purified water to give a suspension and, while maintaining the pH of the suspension at pH 6, an aqueous solution obtained in advance by dissolving 6 g of aluminium chloride hexahydrate in 50 ml of purified water and an aqueous sodium hydroxide solution (10 mass %) were added dropwise each over the period of 10 minutes. Thereafter, while the pH and the temperature of the suspension were maintained continually at pH 6 and 90° C., respectively, stirring was performed for 30 minutes. Thereafter, by washing the filtered solids obtained by filtering the suspension through filter paper with water, a pearlescent pigment was obtained on which a rutile-type titanium dioxide coating and an aluminium hydroxide coating were formed in this order.

Subsequently, 30 g of the pearlescent pigment on which a rutile-type titanium dioxide coating and an aluminium hydroxide coating were formed in this order was added to 0.3 L of purified water. While the temperature of the resulting suspension was maintained at 70° C. with a water bath, 10 g (5 mass %) of a Blue No. 1-containing solution was added to the suspension. Also after the addition of this solution, stirring of the suspension was continued for 15 minutes while maintaining the temperature and the pH of the suspension at 70° C. and pH 6, respectively.

Thereafter, the filtered solids obtained by filtering the suspension through filter paper were dried, and then the filtered solids were subjected to a heat treatment performed in a furnace having a furnace atmosphere temperature of 120° C. for 2 hours. In this manner, the bright pigment of Comparative Example 5 in which a rutile-type titanium dioxide coating and a blue anionic dye-dispersed aluminium hydroxide coating were formed in this order on a scaly glass was obtained. The bright pigment of Comparative Example 5 had a pearlescence with a color created by the combination of the color of the blue dye and a yellow interference color.

Comparative Example 6

The bright pigment of Comparative Example 6 is a pigment with a metallic luster (average particle diameter: 85 μm, average thickness: 1.5 μm) having a structure in which a scaly substrate (a scaly glass substrate, average particle diameter: 80 μm, average thickness: 1.3 μm) is coated with a silver-containing coating composed of silver and an anionic dye-containing hydrotalcite coating (thickness: 50 nm) in this order. The bright pigment of Comparative Example 6 was produced in the following manner.

MC2080PS (manufactured by Nippon Sheet Glass Co., Ltd.) was used as a pigment in which a scaly glass substrate was coated with a silver-containing coating. The silver-containing coating was formed according to an electroless plating method, and the thickness of the silver-containing coating was 40 nm. This pigment had a silver-gray metallic luster and had an average particle diameter of 80 μm and an average thickness of 1.4 μm.

Next, a conditioning solution in which 3 g of aluminium chloride hexahydrate and 5 g of magnesium chloride hexahydrate were dissolved in 50 mL of purified water was prepared. Meanwhile, a suspension was obtained by adding 30 g of MC2080PS and 10 g (10 mass %) of an aqueous Red No. 202-containing solution to 0.3 L of purified water. While the temperature of the resulting suspension was maintained at 75° C. with a water bath, the entire quantity of the conditioning solution was added dropwise to the suspension over 10 minutes. The pH of the suspension was maintained at pH 6 using a 10 mass % aqueous sodium hydroxide solution during the dropwise addition of the conditioning solution. Thereafter, while the pH and the temperature of the suspension were maintained continually at pH 6 and 90° C., respectively, stirring was performed for 30 minutes.

Next, the suspension was filtered through filter paper and the filtered solids were removed, dried, and then subjected to a heat treatment performed in a furnace having a furnace atmosphere temperature of 120° C. for 2 hours. In this manner, the bright pigment of Comparative Example 6 in which a scaly glass substrate was coated with a silver-containing coating and a red anionic dye-containing hydrotalcite coating was obtained. The bright pigment of Comparative Example 6 had a metallic luster casting a red light.

Comparative Example 7

The bright pigment of Comparative Example 7 is a pearlescent pigment (average particle diameter: 42 μm, average thickness: 1.6 μm) having a structure in which a scaly substrate (a scaly glass substrate, average particle diameter: 40 μm, average thickness: 1.3 μm) is coated with a titanium dioxide coating (thickness: 120 nm) and an amorphous calcium phosphate coating (thickness: 50 nm) in this order. The bright pigment of Comparative Example 7 was produced in the following manner.

METASHINE (registered trade name) MC1040RR (manufactured by Nippon Sheet Glass Co., Ltd., pearlescent pigment) was used as a pigment. This has a structure in which a scaly glass substrate is coated with rutile-type titanium dioxide, gives a lustrous red interference color, and has an average particle diameter of 40 μm and an average thickness of 1.5 μm.

485 g of MC1040RR was introduced into 1 liter of ion-exchanged water, 1500 g of a 7.5 mass % aqueous phosphoric acid solution was added while stirring, stirring was performed for 10 minutes to give a suspension, and then the suspension was left to stand still for a whole day and night. The pH of the suspension was measured with a pH meter and found to be 0.1. The scaly glass substrate having a pearlescent luster was separated by suction filtration, and acid treatment was performed.

Next, Suspension A having a solid content concentration of 20% was prepared by adding ion exchange water to the acid-treated scaly glass substrate having a pearlescent luster.

Meanwhile, Calcium hydroxide suspension B in which 11.2 g of calcium hydroxide was dispersed in 1 liter of ion exchange water using a homomixer was prepared, and the Calcium hydroxide suspension B was added to the Suspension A to give an alkali suspension.

Next, while maintaining the fluid temperature of the alkali suspension at 50° C. or lower, 160 g (5 mass %) of an aqueous Red No. 202-containing solution was added first, and the suspension was stirred for 30 minutes while adding a further 7.5 mass % aqueous phosphoric acid solution until a final pH of 6.5 was attained, thereby forming a calcium phosphate coating over a scaly glass substrate. Next, the alkali suspension was subjected to suction filtration, and the resulting filtered solids were dried in a furnace having a furnace atmosphere temperature of 80° C. for 24 hours. In this manner, the bright pigment of Comparative Example 7 in which a scaly glass substrate was coated with a titanium dioxide coating and a red anionic dye-containing amorphous calcium phosphate coating in this order was obtained. The bright pigment of Comparative Example 7 had a pearlescence with a color created by the combination of the color of the red dye and an interference color. The amount of the amorphous calcium phosphate is 3 mass % of the mass of the bright pigment of Comparative Example 7.

Next, lip glosses having the following composition were produced by known means using the bright pigments of Examples 1 to 7 and the Comparative Examples 1 to 7.

| | |
|---|---|
| Dextrin palmitate | 3 parts by mass |
| Hydrogenated polyisobutene | 20 parts by mass |
| Isononyl isooctanoate | 10 parts by mass |
| Squalane | 5 parts by mass |
| Isostearoyl hydrolyzed collagen | 5 parts by mass |
| Sodium hyaluronate | 5 parts by mass |
| Bright pigment of Examples 1 to 7 or Comparative Examples 1 to 7 | 10 parts by mass |

Next, the lip glosses thus obtained were evaluated for beautifying effect, anti-aging effect, and resistance to makeup deterioration (unlikeliness of makeup deterioration to occur) on the lip. Targeted users were 20 female panelists, with the duration of use being four weeks and the frequency of use being 2 times/day.

The beautifying effect was classified according to the number of people who responded "improved lip moisture, tautness and gloss", the anti-aging effect was classified according to the number of people who responded "improved lip chapping, dullness and roughness", and the resistance to makeup deterioration was classified according to the number of people who responded "improvement in the endurance of the effect of sustaining an increased lip volume" as follows.

⊚: 15 people or more
○: 10 to 14 people
Δ: 7 to 10 people
X: 6 people or fewer

TABLE 1

| | Beautifying effect | Anti-aging effect | Resistance to makeup deterioration |
|---|---|---|---|
| Example 1 | ⊚ | ⊚ | ⊚ |
| Example 2 | ⊚ | ⊚ | ⊚ |
| Example 3 | ○ | ○ | ⊚ |
| Example 4 | ⊚ | ⊚ | ⊚ |
| Example 5 | ⊚ | ⊚ | ⊚ |
| Example 6 | ○ | ○ | ⊚ |
| Example 7 | ⊚ | ⊚ | ⊚ |

TABLE 1-continued

|  | Beautifying effect | Anti-aging effect | Resistance to makeup deterioration |
|---|---|---|---|
| Comparative Example 1 | Δ | Δ | X |
| Comparative Example 2 | Δ | X | X |
| Comparative Example 3 | X | X | X |
| Comparative Example 4 | Δ | X | X |
| Comparative Example 5 | Δ | X | X |
| Comparative Example 6 | X | X | X |
| Comparative Example 7 | Δ | Δ | Δ |

Oil Adsorbability of Bright Pigments 4.5 g of oleic acid was added to 0.5 g of the bright pigments of Examples 1 to 7 and Comparative Examples 1 to 7, and left to stand still at a constant temperature of 37° C. for 24 hours to allow the bright pigments to adsorb oleic acid. Moreover, the bright pigments were washed 3 times with 15 ml of diethyl ether and air-dried to give adsorbed samples. Bright pigments onto which no oleic acid was adsorbed (blank samples) and bright pigments onto which oleic acid was adsorbed (adsorbed samples) each were collected in an amount of about 14 to 17 mg, and subjected to a TG-DTA measurement from 30° C. to 600° C. in a nitrogen stream to obtain their oil adsorbency. The rate of temperature increase was 20° C./min.

The difference between the extent of retention (%) upon being heated from 30 to 600° C. (=[weight of sample (600° C.)/weight of sample (30° C.)]×100) and the extent of retention (%) upon being heated from 30 to 150° C. (=[weight of sample (150° C.)/weight of sample (30° C.)]×100) was obtained as the extent of quantity reduction (%), and the difference between the extent of quantity reduction (%) of the blank samples and the extent of quantity reduction (%) of the adsorbed samples was obtained as the extent of adsorption (%). Furthermore, the extent of adsorption (%) was raised to the $10^{th}$ power to obtain the amount of oil adsorption (mg/g). The amount of oil adsorbed is shown in Table 2.

TABLE 2

|  | Amount of oil adsorbed (mg/g) |
|---|---|
| Example 1 | 28 |
| Example 2 | 30 |
| Example 3 | 24 |
| Example 4 | 27 |
| Example 5 | 22 |
| Example 6 | 28 |
| Example 7 | 26 |
| Comparative Example 1 | 3 |
| Comparative Example 2 | 5 |
| Comparative Example 3 | 2 |
| Comparative Example 4 | 3 |
| Comparative Example 5 | 4 |
| Comparative Example 6 | 7 |
| Comparative Example 7 | 25 |

As described above, the present invention can provide a bright pigment having a high oil adsorbability and therefore can provide a cosmetic composition that has good spreadability over, and a good feel upon application to, the outer skin and the surface of a keratinous material and that has high biocompatibility.

Next, a comparative evaluation of the lightfastness of the bright pigments of Example 7 and Comparative Example 7 was performed.

Test Method

Five grams of the bright pigments of Example 7 and Comparative Example 7 were introduced into glass petri dishes in such a manner that each pigment was thinly spread over the bottom. A 48-hour accelerated lightfastness test was performed on the bright pigments in the glass petri dishes using lightfastness testing equipment (Suntest CPS+, manufactured by ATLAS). Using a non-contact spectrocolorimetry system (JX7-100, manufactured by Color Techno System Corporation), $L^*_0$, $a^*_0$, $b^*_0$ before the accelerated lightfastness test and $L^*_{48}$, $a^*_{48}$, $b^*_{48}$ 48 hours past the accelerated lightfastness test were measured according to the L*, a*, b* color system (CIE1976). Then, color changes ΔE*ab were obtained using the formula below.

$$\Delta E^* ab = ((L^*_0 - L^*_{48})^2 + (a^*_0 - a^*_{48})^2 + (b^*_0 - b^*_{48})^2)^{1/2}$$

In contrast to the color change ΔE*ab of the bright pigment of Example 7 of 0.8, the color change ΔE*ab of the bright pigment of Comparative Example 7 was 7.4.

INDUSTRIAL APPLICABILITY

The bright pigment of the present invention has enhanced oil adsorbability and, therefore, a cosmetic composition that has good spreadability over, and a good feel upon application to, the outer skin, the surface of a keratinous material, or the like, that has high biocompatibility, and that is highly resistant to makeup deterioration can be provided. The bright pigment of the present invention is of use as an ingredient of, in particular, nail cosmetics such as nail colors or nail coatings; eyebrow and eye cosmetics such as eye shadows, eyeliners, mascaras or eyebrow colors; pencil-shaped makeup cosmetics such as eyeliner pencils and lipliner pencils; makeup cosmetics such as foundations, blushes, face colors, lipsticks or lip glosses; and makeup cosmetics of a sedimentation type that contain a glittering agent as a sediment in water or a solvent and are shaken appropriately before use.

The invention claimed is:

1. A bright pigment, comprising:
   a flake of a substrate;
   an interference color coating or a silver-containing coating; and
   an outermost coating that covers the flake of a substrate,
   wherein when the bright pigment comprises the interference color coating, the interference color coating (1) covers the flake of a substrate, (2) is disposed between the substrate and the outermost coating and in contact with both the substrate and the outermost coating, and (3) comprises a titanium oxide,
   wherein when the bright pigment comprises the silver-containing coating, the silver-containing coating (1) covers the flake of a substrate, (2) is disposed between the substrate and the outermost coating and in contact with both the substrate and the outermost coating, and (3) comprises silver and/or a silver alloy, and
   wherein the outermost coating is provided as an outermost layer and comprises (1) at least one selected from the group consisting of hydroxyapatite and hydrocalumite, and (2) an anionic pigment.

2. The bright pigment according to claim 1, wherein the outermost coating further comprises at least one member selected from the group consisting of cerium hydroxide and a hydrate of cerium oxide.

3. The bright pigment according to claim 1, wherein the thickness of the outermost coating is 10 nm to 100 nm.

4. The bright pigment according to claim 1, wherein the thickness of the interference color coating is 20 nm to 300 nm.

5. The bright pigment according to claim 1, wherein the thickness of the silver-containing coating is 20 nm to 100 nm.

6. The bright pigment according to claim 1, wherein the silver-containing coating comprises at least one member selected from the group consisting of a silver-gold alloy, a silver-palladium alloy, a silver-platinum alloy, a silver-copper alloy, a silver-gold-palladium alloy, a silver-platinum-palladium alloy, a silver-copper-palladium alloy, a silver-gold-copper alloy and a silver-gold-platinum alloy.

7. The bright pigment according to claim 1, wherein the average particle diameter of the flake of a substrate is 10 μm to 500 μm and the average thickness thereof is 0.3 to 10 μm.

8. A cosmetic composition comprising the bright pigment according to claim 1.

9. The cosmetic composition according to claim 8, further comprising at least one member selected from the group consisting of collagen and hyaluronic acid, and a medium.

\* \* \* \* \*

UNITED STATES PATENT AND TRADEMARK OFFICE
CERTIFICATE OF CORRECTION

Page 1 of 1

PATENT NO. : 9,107,834 B2
APPLICATION NO. : 12/596038
DATED : August 18, 2015
INVENTOR(S) : Kitamura It is certified that error appears in the above-identified patent and that said Letters Patent is hereby corrected as shown below:

In the Specification

Column 3, lines 17-18, delete "silver gold" and insert -- silver-gold --.

Column 3, line 18, delete "silver gold" and insert -- silver-gold --.

Column 5, line 35, delete "silver gold" and insert -- silver-gold --.

Column 21, line 33, delete "C./weight" and insert -- C.)/weight --.

Column 21, line 35, delete "(150° C./weight" and insert -- (150° C.)/weight --.

Signed and Sealed this
Sixteenth Day of February, 2016

Michelle K. Lee
*Director of the United States Patent and Trademark Office*